United States Patent [19]

Hofmann et al.

[11] Patent Number: 4,502,992

[45] Date of Patent: Mar. 5, 1985

[54] PROCESS FOR THE CONTINUOUS PRODUCTION OF ALKYLESTERS OF SATURATED ALIPHATIC CARBOXYLIC ACIDS

[75] Inventors: Peter Hofmann; Hans Regner; Manfred Köppner; Michael Zölffel, all of Marl, Fed. Rep. of Germany

[73] Assignee: Chemische Werke Hüls AG, Marl, Fed. Rep. of Germany

[21] Appl. No.: 376,750

[22] Filed: May 10, 1982

[30] Foreign Application Priority Data

May 16, 1981 [DE] Fed. Rep. of Germany ....... 3119594

[51] Int. Cl.$^3$ ................................................. C11C 3/02
[52] U.S. Cl. ............................. 260/410.9 R; 422/189
[58] Field of Search ................... 260/410.9 C, 410.9 R

[56] References Cited

U.S. PATENT DOCUMENTS

| | | | |
|---|---|---|---|
| 3,507,891 | 4/1970 | Hearne et al. | 260/410.9 C |
| 3,906,016 | 9/1975 | Isa et al. | 260/410.9 R |
| 3,976,670 | 8/1976 | Fanning | 260/410.9 C |
| 4,041,057 | 8/1977 | Fanning | 260/410.9 C |
| 4,320,237 | 3/1982 | Kaufhold et al. | 568/909 |

OTHER PUBLICATIONS

Peter Hofmann et al., "Hydrocarboxymethylation-an Attractive Route from Olefins to Fatty Acid Esters", I & EC, Product Research & Development, vol. 19, 9/1980, pp. 330–334.

*Primary Examiner*—Helen M. S. Sneed
*Attorney, Agent, or Firm*—Wells & Wells

[57] ABSTRACT

A process and apparatus for the continuous production of alkylesters of saturated aliphatic carboxylic acids by reacting olefins with carbon monoxide and alkanol in the presence of a catalyst consisting of a cobalt compound and a promoter selected from the group consisting of pyridine, non-ortho-substituted alkylpyridines and mixtures at elevated pressure and elevated temperature, the reaction based on olefins having at least 8 C atoms and being carried out in a reactor wherein the flow characteristic is adjusted so that tubular flow without back-mixing predominates, and wherein the raw materials are supplied in the desired ratios at the input side of the reactor.

14 Claims, 2 Drawing Figures

PROCESS FOR THE CONTINUOUS PRODUCTION OF ALKYLESTERS OF SATURATED ALIPHATIC CARBOXYLIC ACIDS

CROSS-REFERENCE TO RELATED APPLICATIONS

Applicants claim priority under 35 USC 119 for application No. P 31 19 594.6, filed May 16, 1981 in the Patent Office of the Federal Republic of Germany.

The disclosure of coinventor Hofmann's copending application, Ser. No. 125,482, filed Feb. 28, 1980, and now abandoned and U.S. Pat. Nos. 3,883,587 and 3,935,228 are incorporated herein to show alkoxycarbonylation procedures carried out in the presence of cobalt catalysts and a promoter from the group pyridine, non-ortho-substituted alkylpyridine and mixtures thereof.

Copending U.S. patent application Ser. No. 291,915 filed Aug. 11, 1981 is incorporated herein to show the recirculation of catalyst and promoter.

BACKGROUND OF THE INVENTION

The field of the invention is the production of alkyl esters of saturated aliphatic carboxylic acids and the present invention is particularly concerned with reacting olefins with carbon monoxide and alkanol in the presence of a catalyst consisting of a cobalt compound and a promoter selected from pyridine, non-ortho-substituted alkylpyridine or mixtures thereof at elevated pressures and elevated temperatures.

The state of the art of such alkoxycarbonylation reactions may be ascertained by reference to U.S. Pat. Nos. 3,507,891; 3,906,016; 3,976,670 and 4,041,057 and the article "Hydrocarboxymethylation—an Attractive Route from Olefins to Fatty Acid Esters?" by Peter Hofmann et al as published in I & EC, Product Research & Development, Vol. 19, September 1980, pp. 330–334, the disclosures of which are incorporated herein.

For comparison purposes alkoxycarbonylation is compared in the present invention with hydroformylation as disclosed in U.S. Pat. No. 4,320,237 the disclosure of which is incorporated herein.

It is known that by reacting olefins with carbon monoxide and a compound having a replaceable hydrogen atom such as an alkanol in the presence of a catalyst containing a metal of Group VIII of the Periodic Table of elements and possibly a promoter, fatty acid esters can be produced as disclosed in J. Falbe, Synthesen mit Kohlenmonoxid, Springer, publishers, Berlin, Heidelberg, New York (1967).

A preferred variation of this reaction known as alkoxycarbonylation, is the conversion in the presence of cobalt catalysts. An especially preferred implementation with cobalt catalysts uses additionally pyridine or a non-ortho-substituted alkylpyridine as a promoter as disclosed in U.S. Pat. No. 3,507,891 and U.S. patent application Ser. No. 125,482 filed Feb. 28, 1980.

The alkoxycarbonylation reaction catalyzed by cobalt-pyridine or cobalt pyridine derivatives is similar in its chemistry, its starting materials required for the conversion, the conditions of reaction and the exothermal heat of reaction released, to other carbonylation reactions, in particular the hydroformylation of olefins.

Thus the catalytic cycles of alkoxycarbonylation and hydroformylation differ only in the last stage when the end product is formed. During the aldehyde formation by hydrogenating the C—Co bond of the acyl complex, the ester formation takes place by the alcoholysis of this bond as follows:

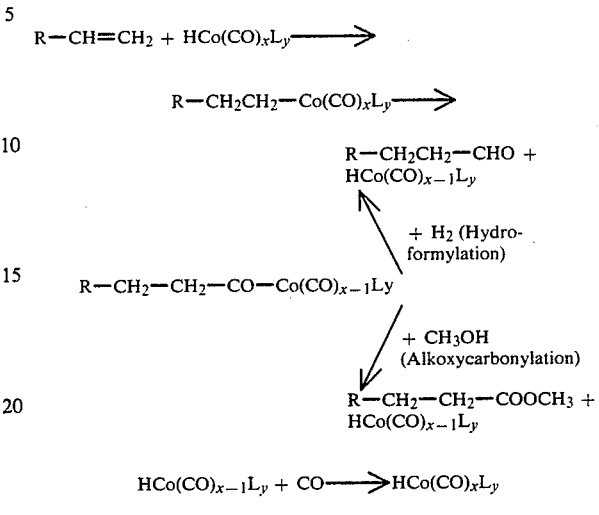

(Catalyst Recovery)

where $x+y=3$ or 4; $L=CO$ or pyridine or a pyridine derivative.

The mixtures of starting materials in alkoxycarbonylation and hydroformylation as a rule consist of those components which will be liquid under the pressures used in the reaction and also those which are still gaseous under these conditions.

Hardly any difference exists regarding optimum pressure and temperature ranges for an alkoxycarbonylation catalyzed by cobalt and pyridine or cobalt and pyridine derivatives and a hydroformylation catalyzed by the same metal. In both cases the conventionally observed temperatures and pressures are within the ranges of 130° to 230° C. and 100 to 300 bars.

Both reactions are exothermal and the particular heats of reaction as a rule are in a range from 28 to 35 kcal/mole.

In view of this wide analogy between these two reactions, it is not surprising that identical reactor designs have been proposed for the continuous, large industrial-scale alkoxycarbonylation and hydroformylation as disclosed in German Pat. No. 926 846, page 2, lines 95 to 117. As a rule these reactors are cylindrical reaction vessels wherein intensive mixing of the reactor contents is achieved by the incorporation of concentric guide pipes and by the introduction of the starting materials, for instance, by high nozzle speed injections at one or several sites along the reactor. A series of steps is known whereby the typical agitation vessel features of the carbonylation reactors are achieved as disclosed by (H. Dubil, J. Gaube, Chem. Ing. Techn. 45 (8), 529–533 [1973]) and in the method of West German Published Application 11 35 879 a liquid is made to circulate by heat convection around a circulation pipe which is freestanding inside the reactor. As regards the method of West German Published Application 10 85 144, the reactor contents are made to circulate by high gas loads using the principle of the air lift pump. In the method of British Pat. No. 1,079,209 the circulation of the liquid is achieved by using an impulsive introduction of the high nozzle-speed reagents. The agitation vessel behavior can also be adjusted by the method of West German Pat. No. 10 03 708, that is by repumping the liquid reactor contents.

Even though reaction losses always had to be incurred as a consequence of the characteristic dwell-time behavior related to the agitated vessel when the above reactor design is maintained in the absence of any special supplemental steps, the reactor with back-mixing has gained widespread use in carrying out carbonylation reactions in industry. A similar process for the production of acetic acid by carbonylating methanol is disclosed in J. Falbe, Synthesen mit Kohlenmonoxid, Springer publishers, Berlin-Heidelberg-New York, 1967, p 118. The heat transfer conditions relating to this reactor having higher flow rates at the cooling surfaces and hence better control of the heat of reaction to be evacuated together with the back-mixing function permit the highest possible temperature constancy throughout the entire reaction space. Specific reaction conditions regarding the temperature of reaction, are assumed to be required for the optimum selectivity of the carbonylation reaction. It is only in the case where several isomeric products are formed that the optimum isomer ratio appears to be adjustable. Lastly a uniform temperature is expected to prevent any catalyst deactivation in zones of local overheating and at the same time also prevents the reaction from "going to sleep" at excessively low temperature sites. The above cited advantages are obtained at the cost of losses in reaction efficiency and of reactors which are more expensive to build.

U.S. Pat. No. 3,976,670 proposes a reactor concept for the continuous implementation of the alkoxycarbonylation reaction whereby it is possible to solve the problem of the heat removal also without back-mixing. In this method the reaction is carried out in a reactor with several intermediary feeders and consists of several segments which increase in diameter toward the end of the reaction tube as shown in FIG. 1 of the patent. The problem of heat evacuation is solved in that the alkanol not only is fed-in together with the other reagents at the beginning of the reactor, but that it also is simultaneously and additionally metered-in along the reactor at several places. Due to the ever limited local feeding of alkanol a more uniform reaction along the entire reactor is expected, and hence also a more uniform heat evacuation or removal and a longer catalyst life.

On the other hand, depending on how the reaction is carried out, the following drawbacks are incurred in the design of U.S. Pat. No. 3,976,670:

(1) Higher capital investment costs are incurred for a high-pressure reactor consisting of several segments of different diameters.

(2) The cost is higher to control the metering a plurality of flows of substances.

(3) In the range of shorter dwell-times which are particularly attractive for industrial applications because of the capacities involved, the reaction rates which are possible in the method of U.S. Pat. No. 3,976,670 are clearly less than the values which are possible using discontinuous batches in agitated autoclaves with simultaneous presence of all the reactants as illustrated in U.S. Pat. No. 3,976,670, at Examples 2 and 3, where single and double stoichiometric quantities of alcohol are added. The comparatively higher reaction rates that might result in the method of the U.S. Pat. No. 3,976,670 at longer dwell times are not economically significant because such a procedure clearly restricts the capacity as illustrated in German Published Application No. 19 63 804, (corresponding to South African Pat. No. 69/8771), page 14, 2nd paragraph.

(4) Lastly the application of the method of U.S. Pat. No. 3,976,670 is unquestionably bound to a clear loss in selectivity. This is so because a restriction on the local alkanol feed leads to an increase of the aldehydes and acetals formed as side products because of the required presence of only low quantities of hydrogen to achieve adequate rates of reaction. This is pointed out by Peter Hofmann et al ibid.; German Published Application No. 19 63 804, claim 1 and U.S. Pat. No. 3,507,891, column 3, lines 63–67.

Reactors permitting a continuous large-scale implementation of exothermal carbonylation processes therefore are designed extensively from the viewpoint of optimum heat evacuation or removal, as indicated above. As a result the above cited limitations and disadvantages will also inevitably follow and be accepted.

SUMMARY OF THE INVENTION

Having in mind the limitations of the prior art it is an object of the present invention to produce alkylesters of saturated aliphatic carboxylic acids by reacting olefins having at least 8 C atoms with carbon monoxide and alkanol in the presence of a catalyst consisting of a cobalt compound and a promoter selected from the group consisting of pyridine, non-ortho-substituted alkylpyridines or mixtures thereof at elevated pressure and elevated temperature so that an optimum compromise regarding the target values determining the commercial success of the alkoxycarbonylation process, namely reaction rate, selectivity and isomer distribution, is achieved.

By elevated temperatures is meant about 80° to 300° C., preferably 150° to 200° C. By elevated pressures is meant carbon monoxide pressures of about 10 to 800, preferably 100 to 300 bars.

This optimum compromise is achieved by a process for the continuous production of alkylesters of saturated aliphatic carboxylic acids by reacting olefins having at least 8 carbon atoms with carbon monoxide and alkanol in the presence of a catalyst consisting of a cobalt compound and a promoter of pyridine, non-ortho-substituted alkylpyridines or a mixture thereof at a pressure of about 10 to 800 bars and a temperature of about 80° to 300° C., the reaction being carried out in a reactor having adjustable flow characteristics where tubular flow without back-mixing is predominant, and wherein the input substances are supplied from the beginning of the reactor in the ratios desired.

The new and unexpected results of the present invention are in that the conditions of the invention require no measures exceeding the norm with respect to heat evacuation or cooling and maintaining a constant reaction temperature as opposed to the methods of the state of the art where a substantial expenditure in apparatus is required and where ponderous drawbacks are incurred. The results of the process of the present invention, which in part rests on carrying out the reaction in a reactor wherein the flow characteristic can be so set that there will be flow through the tube without back-mixing, is furthermore surprising in that it comes about in contradiction to the authoritative opinions held in a predominant number of prior publications: namely the implementation of the carbonylation reaction under optimum back-mixing.

DESCRIPTION OF THE PREFERRED EMBODIMENTS

Figure 1:
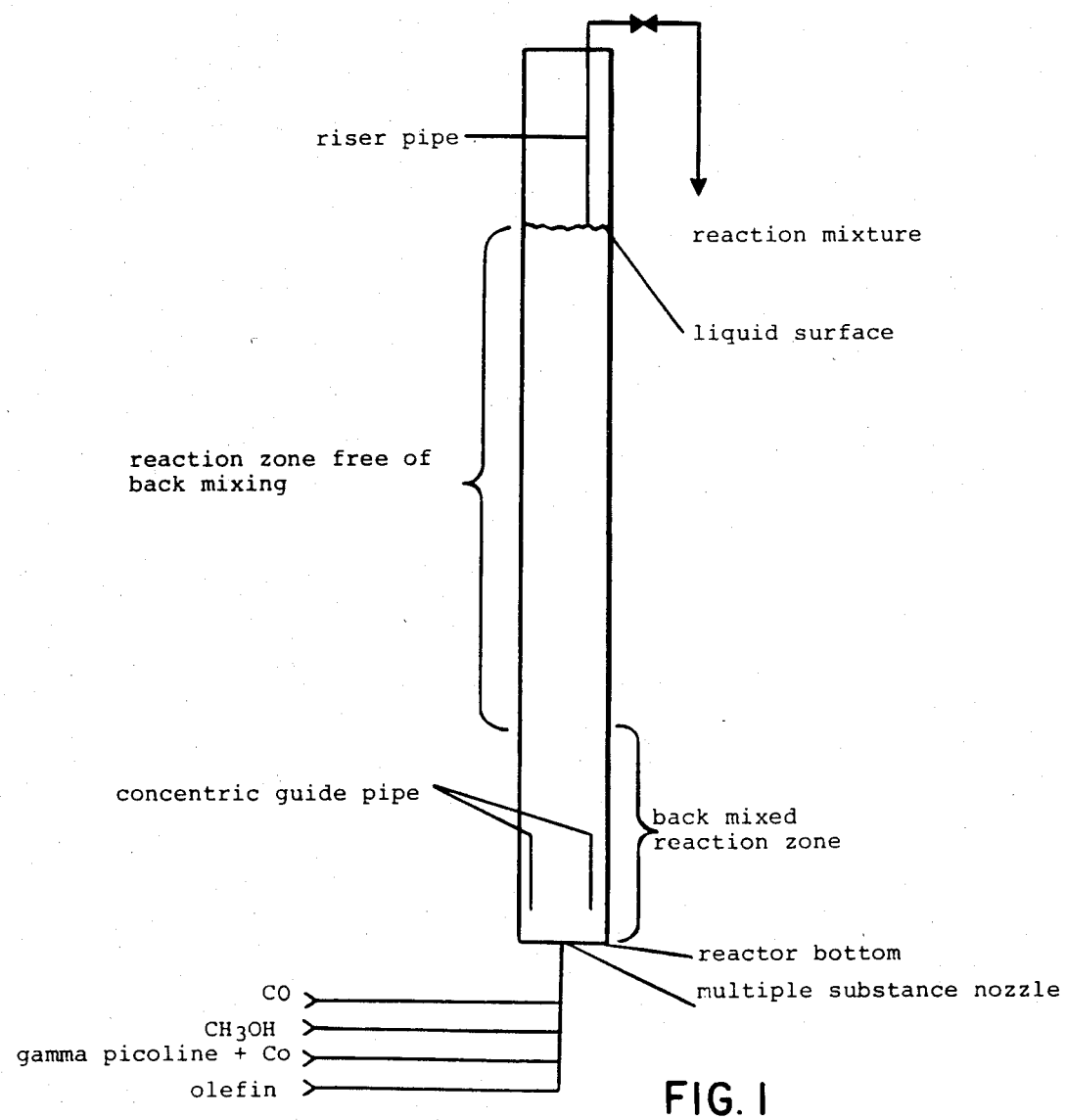
FIG. 1 of the drawings is a view in elevation of the reactor used in Example 2 of the present invention.
Figure 2:
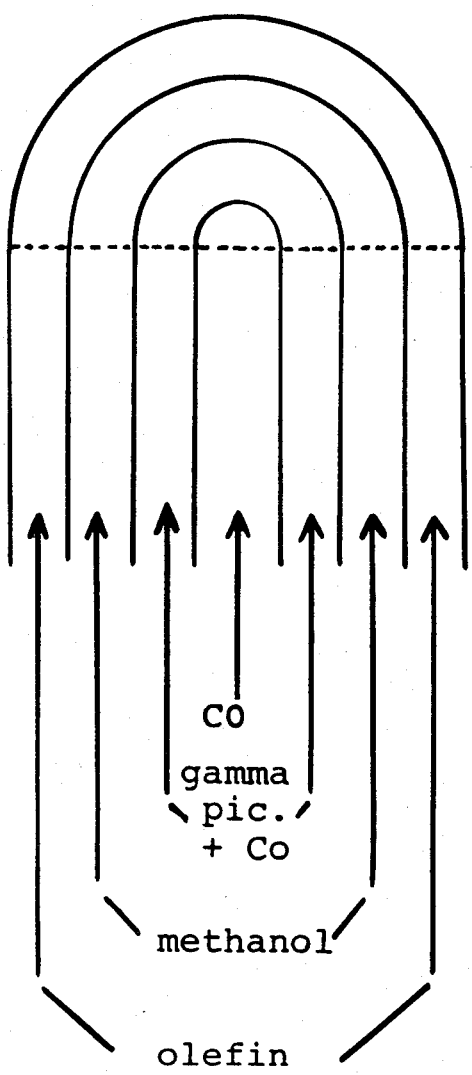
FIG. 2 is a schematic showing of the multiple substance nozzle of FIG. 1.

The process of the present invention is applied in principle to all the alkoxycarbonylation procedures used in the production of carboxylic acid alkylesters wherein a catalyst consisting of a cobalt compound and a promoter of pyridine, non-ortho-substituted alkylpyridine or mixture thereof is used, as for example in the methods of U.S. Pat. No. 3,507,891 and U.S. patent application Ser. No. 125,482. The selection of the type of olefin used is the least critical of all, that is, both straight-chain and branched alpha-olefins as well as olefins with internal double bonds are useful provided they have at least 8 C atoms.

Olefins having 8 to 40, preferably 8 to 20, especially preferred 10 to 18 carbon atoms are used. These olefins are obtained by methods of the state of the art. For instance alpha-olefins are obtained by the Ziegler method of ethylene oligomerization as disclosed in German Pat. No. 878 560 and U.S. Pat. No. 3,310,600 or by wax-cracking olefins with internal double bonds can be obtained by dehydrogenation or chlorination and ensuing dechlorination of paraffins as disclosed in British Pat. No. 1 037 868.

For methods based on paraffins, as a rule three paraffin blends are used, whereby the olefins obtained also lack a uniform C number. In addition all conceivable isomeric forms are obviously present in these olefin mixtures.

Besides pure and possibly substituted olefins, it is possible also to use those with contents having for instance up to 85% by weight in paraffins. There is a paraffin content because incomplete reactions are obtained in the olefin production and the unconverted paraffins are not separated, or are only incompletely separated.

Not only the type of olefin, but also the type of alkanol is not critical for the process of the present invention. Thus both primary and secondary as well as tertiary alkanols having 1 to 20, preferably primary alkanols having 1 to 3 C atoms, such as methanol, ethanol and propanol-(1) are useful.

It is not critical to the process of the present invention which cobalt compound together with the promoter is used as the catalyst. Cobalt carbonyls, for instance dicobaltoctacarbonyl, are just as suitable as carboxylic acid-cobalt salts such as cobalt acetate, cobalt naphthenate and cobalt-2-ethylhexanoate and salts of cobalt with organic acids such as cobalt nitrate and cobalt sulfate. Preferably used are those carboxylic acid cobalt salts in which the anions correspond to the acid group of the carboxylic acid alkylesters formed in the alkoxycarbonylation.

Suitable promoters besides pyridine are all the non-ortho-substituted alkyl pyridines such as 3-picoline and 4-picoline, 3,4-dimethylpyridine, 3,5-dimethylpyridine, 3-ethylpyridine and 4-eithylpyridine, alone or in a mixture.

Appropriately the conditions of reaction for the alkoxycarbonylation are varied depending on the type of olefin being used as disclosed by Peter Hofmann et al. Regardless of the kind of olefin used, the temperature of reaction as a rule is in the range of about 80 to 300, preferably 130° to 230° C. and the carbon monoxide pressure is in the range of about 10 to 800, preferably 100 to 300 bars.

Further, except for carbon monoxide, the ratios of the materials used are as follows:

(a) cobalt/olefin=from about 0.002 to 0.3, preferably 0.005 to 0.1 gram-atom of cobalt per mole of olefin;

(b) promoter: cobalt=from about 2 to 100, preferably 5 to 50 moles of promoter per gram-atom of Co; and (c) alkanol/olefin=from 1 to 20, preferably 1 to 10 moles of alkanol per mole of olefin.

The carbon monoxide may contain up to 10, preferably 5% by volume of hydrogen and is supplied appropriately in an amount together with the input substances already cited so that the consumption of gases caused by the reaction and any removal of waste gases are compensated for. As a rule the process of the present invention is implemented using from at least the stoichiometric amount of carbon monoxide, to at most double the stoichiometric amount as referred to the converted olefin.

In addition to the already cited partial step of using olefins having at least 8 C atoms, the process of the present invention is critically susceptible to that partial step whereby the starting materials are supplied in the desired or required ratios from the beginning. This step excludes the implementation of alkoxycarbonylation in those reactors where one or more starting materials are fed in along the length of the reactor at positions of different reaction rates such as in the method of the U.S. Pat. No. 3,976,670.

Lastly the process of the present invention is critically susceptible to the partial step of the continuous alkoxycarbonylation reaction being carried out in such a reactor as permits the adjustment of the flow characteristics so that the flow in the tube takes place predominantly without back-mixing. This means that tubular flow characteristics free from back-mixing must exist in at least 50% of the reactor volume filled with liquid. The publication of Walter Broetz, Grundriss der chemischen Reaktionstechnik, Chemie publishers, Weinheim, 1958, pp 300 is incorporated herein to show the details of reactor flow characteristics.

This does not exclude the presence on a minor scale of other flow characteristics in the reactor, for instance turbulent flow. Flow conditions deviating from tubular flow may occur especially in the region of raw material feed-in.

The typical reactor for the process of the invention as shown in the figure of the drawing is a cylindrical, vertically standing tubular reactor. The ratio of length to diameter of such a reactor ranges from about 500:1 to 3:1, but preferably is within 50:1 to 5:1.

The raw materials which include olefin, alkanol, carbon monoxide and catalyst are appropriately fed in at the intake, that is through the reactor bottom. Devices such as multiple-material nozzles, sieve plates and annular tubular conduits parallel to the bottom and with several discharge apertures can be used for input. To achieve better mixing of the initial materials and of any reaction products already present, the tubular flow without back-mixing in the lower portion of the reactor, where this lower portion is less than 50% of the the reactor volume filled with liquid, can be replaced by another flow characteristic. This can be achieved for instance by installing concentric internal pipes. When an internal pipe is used, this pipe appropriately does not protrude beyond the lower third of the liquid-filled reactor volume, and the input materials are fed in through the nozzles at a rate which ensures a liquid circulation around the internal pipe.

The evacuation or removal of the heat of reaction being released in the reactor is implemented both by cooling means built into the reaction space and by surface cooling of the reactor. Especially when there are back-mixing conditions of flow in the lower part of the reactor, it is appropriate to evacuate the heat of reaction being developed by introducing cold input materials through cooling coils where $T_{input\ materials} < T_{reaction\ mixture}$.

It has been found particularly advantageous in relation to the present process as disclosed in U.S. patent application Ser. No. 291,915, to treat the reaction mixture after the reaction with an oxygenated gas and to remove the unconverted alkanol and olefin, the promoter and the reaction products by distillation, to absorb the distillation residue, in pyridine, a non-ortho-substituted alkylpyridine, or promoter mixture to treat the cobalt suspension so obtained by absorbing the residue in the promoter with a mixture of carbon monoxide and hydrogen containing from 10 to 90% by volume of hydrogen at a temperature of 100° to 250° C. and at a pressure of at least 50 bars, and to feed the catalyst solution so obtained back into the process.

The specific Examples which follow illustrate the process of the present invention:

COMPARISON TEST A

A mixture containing 29.5 parts by weight of cobalt naphthenate with a content of 10% by weight of cobalt and 46.5 parts by weight of gamma-picoline and following preformation by reaction with synthesis gas (consisting of equal parts of $H_2$ and CO) at 170°C., 160 bars and an average dwell time of 0.5 h together with 168 parts by weight of a statistical isomer mixture of internal double bonded n-dodecenes (with an alpha portion less than 1%) and 64 parts by weight of methanol and carbon monoxide is passed through a mixing nozzle at the bottom of a vertically standing cylindrical reactor.

A loop-shaped liquid circulation is generated by means of a guide pipe concentrically arranged inside the reactor, beginning at the reactor bottom and terminating below the liquid level, around this guide pipe and inside the reactor. The intake rate of the reagents is adjusted high enough that besides intense dispersion of the gaseous component, the circulating liquid flow rate is about 10 times the intake rate on account of the impulsive feed-in.

The reaction takes place at a temperature of 180° C. and a pressure of 170 bars for an average dwell time of 1.9 h, the heat of reaction developed being evacuated by cooling coils suspended within the reactor.

Under these conditions, 63.0% of the input olefin are converted, at a selectivity of 97% referred to the ester formation and for an n-ester proportion of 74%.

EXAMPLE 1

Comparison test A is repeated except that the reactor for the alkoxycarbonylation is operated without a guide pipe, that is, while extensively avoiding back-mixing. The olefin conversion is 80.4% for an ester selectivity of 98% and an n-ester proportion of 74%.

EXAMPLE 2

The conditions of reaction regarding temperature, pressure and input quantities are established as in example 1. The upper part of the guide pipe of Comparison test A is so shortened as shown in FIG. 1 of the drawing that the liquid circulates only in the lower reactor part amounting to about 30% of the total reactor volume and at a roll-over rate about ten times that of the input rate. An olefin conversion of 78.9% is achieved with a selectivity of 98.5% for esters with an n-proportion of 75%.

COMPARISON TEST B

A mixture of 10 parts by weight of cobalt naphthenate with a cobalt content of 10 parts by weight and 44.7 parts by weight of pyridine following preformation under the conditions of comparison test A together with 81 parts by weight of n-octene (1) and 32.3 parts by weight of methanol as well as carbon monoxide is fed through the mixing nozzle at the bottom of a reactor. The reactor design and operation are the same as for comparison test A.

The reaction takes place at a temperature of 150° C. and a pressure of 135 bars for a mean dwell time of 1.3 h. Under these conditions an olefin conversion of 64.6% is obtained with a selectively of 98% and an n-ester proportion of 84%.

EXAMPLE 3

Comparison test B is repeated except that the reactor for the alkoxycarbonylation is operated without a guide pipe, that is, while extensively avoiding back-mixing. 77.3% of the olefins fed-in are converted with an ester selectivity of 98%, the n-proportion of these esters being 84.5%.

EXAMPLE 4

The conditions of reaction regarding the temperature, pressure and the input quantities are established as in example 3. The guide pipe of comparison test A is so shortened at the top that the liquid circulates only in the lower part of the reactor amounting to about 45% of the total reactor contents and circulating at a roll-over rate ten times that of the input rate. The resulting olefin conversion is 76.6% with a selectively of 98.3% regarding ester formation and an n-ester proportion of 84.7%.

We claim:

1. In a process for the continuous production of alkylesters of saturated aliphatic carboxylic acids by reacting starting materials comprising olefins with carbon monoxide and alkanol in the presence of a catalyst consisting of a cobalt compound and a promoter selected from the group consisting of pyridine, non-ortho-substitued alkylpyridines and mixtures thereof at elevated carbon monoxide pressures and elevated temperatures in a reactor having an input side, the improvement comprising:

said olefins having at least 8 carbon atoms and carrying out the reaction in said reactor comprising a single, cylindrical vertical tube and having tubular flow without back-mixing, and feeding said raw materials in given reaction ratios into said input side of said reactor.

2. The process of claim 1, wherein said given reaction ratios are 0.002-0.3 gram atoms of cobalt/mole of olefin, 2-100 moles of promoter/gram atom of cobalt, and 1-20 moles of alkanol/mole of olefin.

3. The process of claim 1, wherein said given reaction ratios are 0.005–0.1 gram atoms of cobalt/mole of olefin, 5–50 moles of promoter/gram atom of cobalt, and 1–10 moles of alkanol/mole of olefin.

4. The process of claim 2, wherein said carbon monoxide pressures are 10 to 800 bars and said elevated temperatures are 80° to 300° C.

5. The process of claim 3, wherein said carbon monoxide pressures are 100 to 300 bars and said elevated temperatures are 130° to 230° C.

6. The process of claim 4, wherein said olefins have 8–40 carbon atoms.

7. The process of claim 4, wherein said olefins have 8–20 carbon atoms.

8. The process of claim 5, wherein said olefins have 10 to 18 carbon atoms.

9. The process of claim 8, wherein said alkanol has 1 to 3 carbon atoms.

10. The process of claim 9, wherein said reactor has a ratio of length to diameter of 500:1 to 3:1.

11. The process of claim 9, wherein said reactor has a ratio of length to diameter of 50:1 to 5:1.

12. The process of claim 11, wherein said cobalt compound suspended in said promoter is subjected, prior to being fed into the reactor, to a treatment at elevated pressures and elevated temperatures with a mixture of carbon monoxide and hydrogen.

13. In a process for the continuous production of alkylesters of saturated aliphatic carboxylic acids by reacting starting materials comprising olefins with carbon monoxide and alkanol in the presence of a catalyst consisting of a cobalt compound and a promoter selected from the group consisting of pyridine, non-ortho-substituted alkylpyridines and mixtures thereof at elevated carbon monoxide pressures and elevated temperatures in a reactor having an input side, the improvement comprising:

said olefins having at least 8 carbon atoms and carrying out the reaction in said reactor having tubular flow and a back-mixing flow is deliberately established in a region of said input side of said reactor, said region being less than 50 percent of the reactor space and feeding said raw materials in given reaction ratios into said input side of said reactor.

14. The process of claim 13, wherein said given reaction ratios are 0.005–0.1 gram atoms of cobalt/mole of olefin, 5–50 moles of promoter/gram atom of cobalt and 1–10 moles of alkanol/mole of olefin, said carbon monoxide pressures are 100 to 300 bars, said elevated temperatures are 130° to 230° C., said olefins have 8–20 carbon atoms, said alkanol has 1 to 3 carbon atoms, and said reactor has a ratio of length to diameter of 50:1 to 5:1.

* * * * *